US011291701B1

(12) United States Patent
Gonzalez

(10) Patent No.: US 11,291,701 B1
(45) Date of Patent: Apr. 5, 2022

(54) ORALLY DISINTEGRATING, SUBLINGUAL AND BUCCAL FORMULATIONS

(71) Applicant: Danny S. Gonzalez, San Francisco, CA (US)

(72) Inventor: Danny S. Gonzalez, San Francisco, CA (US)

(73) Assignee: SEED EDIBLES, San Francisco, CA (US)

( * ) Notice: Subject to any disclaimer, the term of this patent is extended or adjusted under 35 U.S.C. 154(b) by 0 days.

(21) Appl. No.: 17/353,149

(22) Filed: Jun. 21, 2021

Related U.S. Application Data

(60) Provisional application No. 63/145,578, filed on Feb. 4, 2021.

(51) Int. Cl.
| *A61K 36/185* | (2006.01) |
| *A61K 9/00* | (2006.01) |
| *A61K 31/352* | (2006.01) |
| *A61K 31/05* | (2006.01) |
| *A61K 9/20* | (2006.01) |
| *A61K 31/045* | (2006.01) |

(52) U.S. Cl.
CPC .......... *A61K 36/185* (2013.01); *A61K 9/0056* (2013.01); *A61K 9/2009* (2013.01); *A61K 9/2013* (2013.01); *A61K 9/2018* (2013.01); *A61K 9/2072* (2013.01); *A61K 31/045* (2013.01); *A61K 31/05* (2013.01); *A61K 31/352* (2013.01)

(58) Field of Classification Search
None
See application file for complete search history.

(56) References Cited

U.S. PATENT DOCUMENTS

| 6,376,545 B1 * | 4/2002 | Levin | A61P 25/16 514/567 |
|---|---|---|---|
| 2001/0053778 A1 * | 12/2001 | Hoover | A61P 3/06 514/227.8 |
| 2008/0317853 A1 * | 12/2008 | Kashid | A61K 31/54 424/465 |
| 2009/0317488 A1 * | 12/2009 | Mehta | A61K 33/26 424/648 |
| 2010/0111902 A1 * | 5/2010 | Durfee | A61P 19/10 424/85.5 |
| 2011/0014132 A1 * | 1/2011 | Liu | A61P 1/14 424/43 |
| 2016/0015683 A1 * | 1/2016 | McCarty | A61K 31/05 514/733 |
| 2016/0296464 A1 * | 10/2016 | Lindsay | A61K 9/0053 |
| 2019/0336554 A1 * | 11/2019 | Li | A23L 27/88 |
| 2020/0022945 A1 * | 1/2020 | Swartout | A61K 31/352 |
| 2020/0376057 A1 * | 12/2020 | Hansen | A61K 47/38 |

FOREIGN PATENT DOCUMENTS

| GB | 902369 | * | 8/1962 | |
| WO | WO-2016092539 A1 | * | 6/2016 | A61K 9/2009 |

* cited by examiner

*Primary Examiner* — Aradhana Sasan
(74) *Attorney, Agent, or Firm* — Polsinelli PC; J. Morgan Kirley; Ron Galant

(57) ABSTRACT

The present invention is related to an orally disintegrating, sublingual or buccal formulation of active ingredient such as cannabidiol or tetrahydrocannabinol.

16 Claims, 1 Drawing Sheet

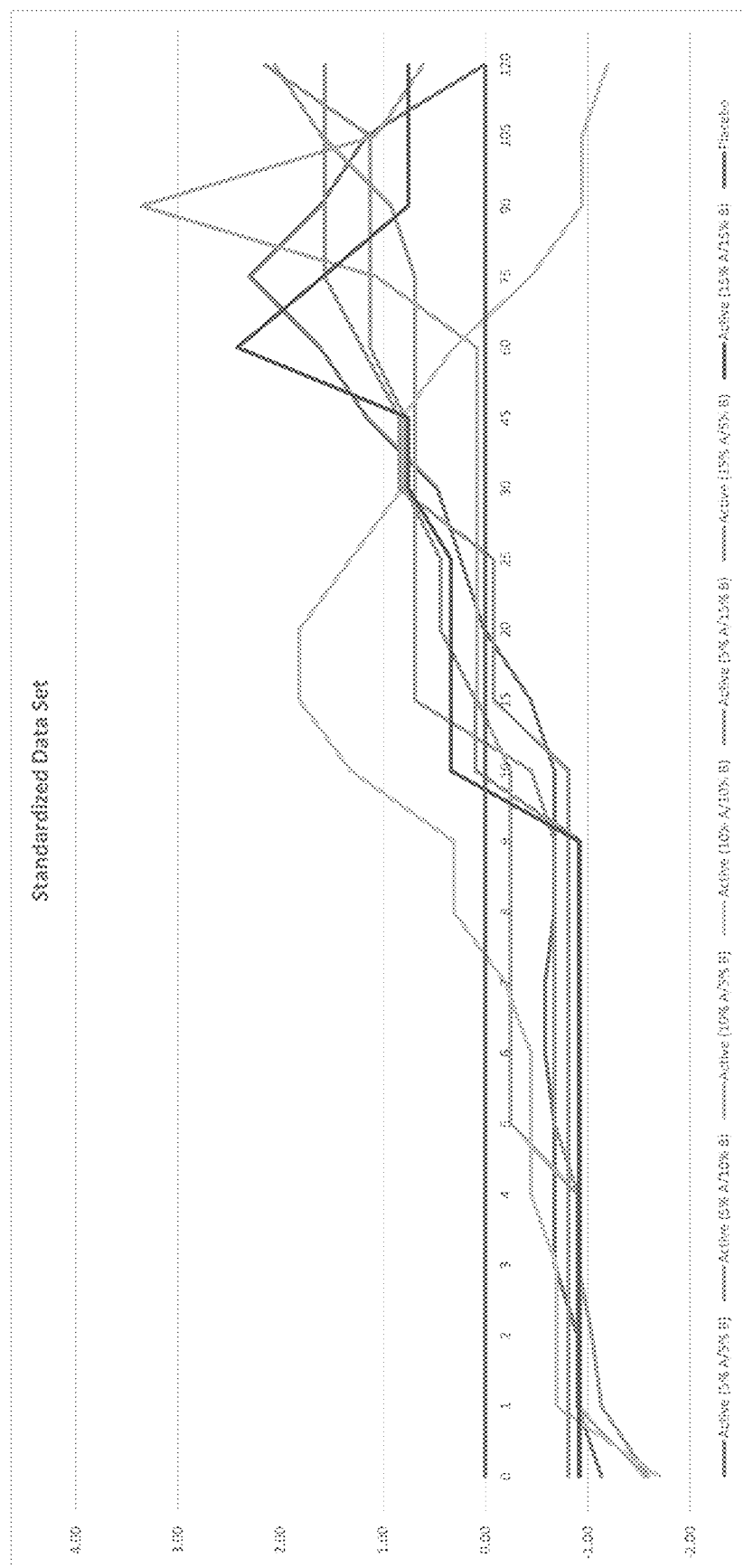

ORALLY DISINTEGRATING, SUBLINGUAL AND BUCCAL FORMULATIONS

FIELD OF THE INVENTION

Provided herein is an orally disintegrating, sublingual or buccal formulation of an active ingredient such as cannabidiol or tetrahydrocannabinol.

BACKGROUND OF THE INVENTION

Active ingredients such as cannabidiol (CBD) and tetrahydrocannabinol (THC) may be helpful in providing relief for conditions including pain, decreasing opioid use, anxiety, epilepsy, glaucoma, HIV/AIDS symptoms, Irritable Bowel Syndrome, movement disorders such as Tourette Syndrome, Multiple Sclerosis, nausea and vomiting associated with chemotherapy, posttraumatic stress disorder, and sleep problems, and also have recreational uses. CBD and THC can be formulated into oral dosage forms, including chewable forms exemplified by gellans/gelatins like gummies, mints, and cookies. But ingesting the active ingredients in this form exposes them to the gastric contents and to first pass metabolism. This can result in inconsistent dosing and delayed and unpredictable onset of effects. This may be due to one or more of lipophilic interactions, dilution of the active ingredients, or degradation of the active ingredients. Accordingly, there is a need in the art for improved oral dosage formulations.

SUMMARY OF THE INVENTION

Provided herein is a dosage form, which may be oral. The dosage form may be orally disintegrating, buccal, or sublingual. The dosage form may contain (a) about 0.5 to 3% wt/wt of a sweetener; (b) about 6.5 to 20% wt/wt citric acid, oleic acid, caprylic acid, tartaric acid, or succinic acid; (c) about 6.5 to 20% wt/wt sodium bicarbonate, potassium bicarbonate, or potassium carbonate; (d) about 1 to 5% wt/wt sodium carbonate or calcium carbonate; (e) about 25 to 35% wt/wt silicon dioxide or calcium phosphate; (f) about 5 to 10% wt/wt cellulose, lecithin, corn starch, potato starch, pectin, or agar; (g) about 25 to 35% wt/wt dibasic calcium phosphate anhydrous; (h) about 0.5 to 1% wt/wt menthol extract; (i) about 2.5 to 7% wt/wt potassium hydrogen tartrate; and, (j) about 0.5 to 1.5% wt/wt active ingredient.

The active ingredient may be tetrahydrocannabinol (THC) extract, cannabidiol (CBD) extract, an analog of the foregoing, a derivative of the foregoing, or a combination thereof. In particular, the active ingredient may be one or more of THC extract, CBD extract, tetrahydrocannabinolic acid (THCa) extract, and cannabidiolic acid (CBDa) extract. Even more particularly, the active ingredient may be THC. The sweetener may be mannitol, sorbitol, xylitol, lactitol, erythritol, or a combination thereof. The sweetener may be mannitol. The oral dosage form may contain citric acid. The oral dosage form may also contain sodium bicarbonate. The oral dosage form may contain sodium carbonate. The oral dosage form may also contain silicon dioxide. The oral dosage form may contain cellulose. The menthol extract may be menthol oil (0.3 mg).

The oral dosage form may contain mannitol, citric acid, sodium bicarbonate, sodium carbonate, silicon dioxide, cellulose, dibasic calcium phosphate anhydrous, menthol oil (0.3 mg), potassium hydrogen tartrate, and THC. In particular, the oral dosage form may contain (a) about 3% wt/wt mannitol; (b) about 15% wt/wt citric acid; (c) about 15% wt/wt sodium bicarbonate; (d) about 5% wt/wt sodium carbonate; (e) about 25% wt/wt silicon dioxide; (f) about 5% wt/wt cellulose; (g) about 25% wt/wt dibasic calcium phosphate anhydrous; (h) about 0.75% wt/wt menthol oil (0.3 mg); (i) about 5% wt/wt potassium hydrogen tartrate; and, (j) about 1.25% wt/wt THC extract.

The oral dosage form may be a solid tablet or powder, and in particular may be a solid tablet. The oral dosage form may also be effervescent when dissolved in an aqueous solution.

Further provided herein is an orally disintegrating, sublingual, or buccal dosage form that consists of (a) 3% wt/wt mannitol; (b) 15% wt/wt citric acid; (c) 15% wt/wt sodium bicarbonate; (d) 5% wt/wt sodium carbonate; (e) 25% wt/wt silicon dioxide; (f) 5% wt/wt cellulose; (g) 25% wt/wt dibasic calcium phosphate anhydrous; (h) 0.75% wt/wt menthol extract; (i) 5% wt/wt potassium hydrogen tartrate; and, (j) 1.25% wt/wt THC extract. The menthol extract may be menthol oil (0.3 mg). The dosage form may be a solid tablet. The dosage form may also be effervescent when dissolved in an aqueous solution.

BRIEF DESCRIPTION OF THE DRAWINGS

FIG. 1 shows the timing of the effects of an active ingredient formulated in an oral formulation described herein.

DETAILED DESCRIPTION

The inventor has discovered that the formulations described herein surprisingly provide rapid and improved uniformity of delivery of an active ingredient such as CBD and/or THC or an analog thereof. The formulation in particular provides advantages over other oral formulations such as gelatin/gellan formulations ("gummies"), mints, and cookies. Specifically, the inventors have discovered orally disintegrating, buccal, and sublingual formulations that avoid exposure of the active ingredients to the gastric contents and first pass metabolism, and the concomitant negative effects on delivery of the actives to their sites of action. Without being bound by theory, the formulations described herein provide rapid and consistent delivery of CBD and/or THC (or analogs or derivatives thereof) as compared to known oral formulations by avoiding negative impacts on peak concentrations, metabolic byproducts, and delayed onset of effects. The formulations described herein improve the amount of active ingredients absorbed and the rate of absorption. The improvements exhibited by the oral formulations may be due to their effervescent characteristics.

1. Definitions

The terminology used herein is for the purpose of describing particular embodiments only and is not intended to be limiting. As used in the specification and the appended claims, the singular forms "a," "an" and "the" include plural referents unless the context clearly dictates otherwise.

For recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9, and 7.0 are explicitly contemplated.

"About" as used herein may mean +/−15% of a recited value or amount. For amounts measured in % wt/wt, "about"

may mean +/−10% of the percentage points recited. For example, about 5% wt/wt may mean 4.5-5.5%.

2. Oral Formulation

Provided herein is an oral formulation comprising an active ingredient, which may be one or more of CBD, THC, an analog thereof, a derivative thereof, and a combination of the foregoing. In one example, the THC comprises at least one of tetrahydrocannabinol and delta-9-tetrahydrocannabinol (delta-9-THC). In another example, the THC is delta-9-THC. In one example, the analog is cannabidiolic acid (CBDa) or tetrahydrocannabinolic acid (THCa). In another example, the analog is selected from cannabinol (CBN), cannabigerol (CBG), cannabichromene (CBC), cannabicyclol (CBL), cannabivarin (CBV), tetrahydrocannabiorcol (THCC), tetrahydrocannabivarin (THCV), tetrahydrocannabiphorol (THCP), cannabidivarin (CBDV), cannabichromevarin (CBCV), cannabigerovarin (CBGV), cannabigerol monomethyl ether (CBGM), cannabielsoin (CBE), and cannabicitran (CBT).

The formulation may be orally disintegrating, sublingual, or buccal. The formulation may also be effervescent. The formulation may be a powder or a solid. In one example, the solid formulation is a tablet. The solid tablet may comprise channels or perforations to increase surface area, which may provide more rapid absorption of the active ingredient. The optimal pH for the formulation, which may provide enhanced transport across the mucosa, may be about 4.5, 5, 5.5, 6.0, 6.5, or a range thereof. In one example, the optimal pH is about 4.5-6.5.

Without being bound by theory, surface charges of the active ingredient may limit the efficiency of transport through the mucosa. In addition, the lipophilic nature of the active product may limit its solubility in saliva, which may in turn limit absorption of the active ingredient. The formulations described herein addresses these limitations by creating a favorable micro-environment for dissolution of the active ingredient by including citric acid to create an environment favoring the dissolution of the active ingredient in an aqueous environment. The formulation may also promote transport of the active ingredient through the mucosa by creating a basic environment to support favorable transport of lipophilic cannabinoid molecules across the mucosa.

The oral formulation may provide an onset of effect for the active ingredient at about 1, 2, 3, 4, 5, 6, 7, 8, 9, 10, 11, 12, 13, 14, 15, 16, 17, 18, 19, or 20 minutes after being ingested, or a range thereof. In one example, the onset of effect is at less than 3, 4, or 5 minutes. The effect may be one or more of increased relaxation, altered perception, increased appetite as perceived by the user (based on results of Kleinloog, Profiling the subjective effects of Δ9-tetrahydrocannabinol using visual analogue scales (2014)), or a combination thereof.

The oral formulation may also provide a peak concentration or a peak effect for the active ingredient at about 10, 20, 30, 40, 50, 60, 70, 80, 90, 100, 110, or 120 minutes after being ingested, or a range thereof. In one example, the peak concentration or effect may be at about 30 minutes. In comparison, oral formulations known in the art have an onset of effect at about 1-2 hours and a peak effect at 1-8 hours after ingestion. An effective amount, which may be a therapeutically effective amount, of the active ingredient may cross into the blood of a subject in less than about 1, 2, 3, 4, 5, 6, 7, 8, 9, 10, 12, 13, 14, 15, 16, 17, 18, 19, or 20 minutes after ingestion of the oral formulation, or a range thereof. In one example, the effective amount crosses the mucosal membrane in less than about 3-5 minutes. The active ingredient may cross into the blood by mucosal absorption in the oral cavity, absorption through the gastrointestinal mucosa after being swallowed, or a combination thereof.

a. Active Ingredient

The active ingredient may be in an oil form. In another example, the active ingredient is a solid, free-flowing powder. In one example, the formulation contains about 0.5 to 1.5% wt/wt of the active ingredient, particularly about 0.50, 0.55, 0.60, 0.65, 0.70, 0.75, 0.80, 0.85, 0.90, 0.95, 1.00, 1.05, 1.10, 1.15, 1.20, 1.25, 1.30, 1.35, 1.40, 1.45, or 1.50% wt/wt, or a range thereof. The formulation may comprise about 1.25% wt/wt THC and/or CBD extract.

b. Core Component Mix

The formulation may comprise a core component mix, which may comprise one or more inactive ingredients. The inactive ingredients may comprise one or more of citric acid, oleic acid, caprylic acid, tartaric acid, succinic acid, sodium carbonate, calcium carbonate, sodium bicarbonate, dibasic calcium phosphate anhydrous, menthol extract, and potassium hydrogen tartrate. The inactive ingredients may comprise at least two components that are capable of producing effervescence when dissolved in an aqueous solution. For example, the inactive ingredients may comprise a soluble acid source and a carbon dioxide source. In one example, the source of soluble acid is citric acid. In another example, the carbon dioxide source is sodium carbonate, calcium carbonate, or sodium bicarbonate.

The citric acid may be present at about 6.5 to 20% wt/wt, particularly about 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, or 20.0% wt/wt, or a range thereof. In one example, the formulation comprises about 15.0% wt/wt citric acid. In another example, the citric acid may be substituted with one or more of oleic acid, caprylic acid, tartaric acid, and succinic acid.

The sodium bicarbonate may be present at about 6.5 to 20% wt/wt, particularly about 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, or 20.0% wt/wt, or a range thereof. In one example, the formulation comprises about 15.0% sodium bicarbonate. In another example, the sodium bicarbonate may be substituted with one or more of sodium bicarbonate, sodium carbonate, potassium bicarbonate, and potassium carbonate.

The sodium carbonate and/or calcium carbonate may be present at about 1 to 5% wt/wt, particularly about 1.0, 1.5, 2.0, 2.5, 3.0, 3.5, 4.0, 4.5, or 5.0% wt/wt, or a range thereof. In one example, the formulation comprises about 5.0% wt/wt sodium carbonate and/or calcium carbonate, and sodium carbonate in particular.

The dibasic calcium phosphate anhydrous may be present at about 25 to 35% wt/wt, particularly about 25.0, 25.5, 26.0, 26.5, 27.0, 27.5, 28.0, 28.5, 29.0, 29.5, 30.0, 30.5, 31.0, 31.5, 32.0, 32.5, 33.0, 33.5, 34.0, 34.5, or 35.0% wt/wt, or a range thereof. In one example, the formulation comprises about 25.0% wt/wt dibasic calcium phosphate anhydrous.

The menthol extract, which may be menthol oil (0.3 mg), may be present at about 0.5 to 1.0% wt/wt, particularly about 0.50, 0.55, 0.60, 0.65, 0.70, 0.75, 0.80, 0.85, 0.90, 0.95, or 1.0% wt/wt, or a range thereof. In one example, the formulation comprises 0.75% wt/wt menthol extract, particularly menthol oil (0.3 mg).

The potassium hydrogen tartrate may be present at about 2.5 to 7.0% wt/wt, particularly about 2.5, 3.0, 3.5, 4.0, 4.5, 5.0, 5.5, 6.0, 6.5, or 7.0% wt/wt, or a range thereof. In one example, the formulation comprises about 5.0% wt/wt potassium hydrogen tartrate.

c. Additional Excipients

The formulation may comprise an additional excipient, which may be one or more of silicon dioxide, calcium phosphate, and cellulose. In one example, silicon dioxide and/or calcium phosphate is present at about 25 to 35% wt/wt, particularly about 25.0, 25.5, 26.0, 26.5, 27.0, 27.5, 28.0, 28.5, 29.0, 29.5, 30.0, 30.5, 31.0, 31.5, 32.0, 32.5, 33.0, 33.5, 34.0, 34.5, or 35.0% wt/wt, or a range thereof. In one example, the formulation comprises about 25.0% wt/wt silicon dioxide and/or calcium phosphate, and particularly silicon dioxide.

In one example, cellulose is present at about 5 to 10% wt/wt, particularly about 5.0, 5.5, 6.0, 6.5, 7.0, 7.5, 8.0, 8.5, 9.0, 9.5, or 10.0% wt/wt, or a range thereof. In one example, the formulation comprises about 5.0% cellulose. The cellulose may be substituted with one or more of lecithin, corn starch, potato starch, pectin, and agar.

d. Sweetener

The formulation may comprise a sweetener, which may be at least one of mannitol, sorbitol, xylitol, lactitol, erythritol, sucrose, and dextrose. The formulation may comprise about 0.5 to 3% wt/wt sweetener, particularly about 0.50, 0.55, 0.60, 0.65, 0.70, 0.75, 0.80, 0.85, 0.90, 0.95, 1.00, 1.05, 1.10, 1.15, 1.20, 1.25, 1.30, 1.35, 1.40, 1.45, 1.50, 1.55, 1.60, 1.65, 1.70, 1.75, 1.80, 1.85, 1.90, 1.95, 2.00, 2.05, 2.10, 2.15, 2.20, 2.25, 2.30, 2.35, 2.40, 2.45, 2.50 2.55, 2.60, 2.65, 2.70, 2.75, 2.80, 2.85, 2.90, 2.95, or 3.00% wt/wt, or a range thereof. In one example, the sweetener is mannitol. In another, the formulation comprises about 3% wt/wt mannitol.

Additional examples of the formulation are provided in the table below.

TABLE 1

| Role | Ingredient | Alternative(s) | Amount (% wt/wt) | Exemplary Amount (% wt/wt) |
|---|---|---|---|---|
| Sweetener | Mannitol | sorbitol, xylitol, lactitol, elythritol, sucrose, dextrose | 0.5-3 | 3.00 |
| Core component mix | Citric acid | oleic acid, caplylic acid, tartaric acid, succinic acid | 6.5-20 | 15.00 |
| Core component mix | Sodium bicarbonate | sodium carbonate, potassium bicarbonate, potassium carbonate | 6.5-20 | 15.00 |
| Core component mix | Sodium carbonate | calcium carbonate | 1-5 | 5.00 |
| Excipient | Silicon dioxide | calcium phosphate | 25-35 | 25.00 |
| Excipient | Cellulose | lecithin, corn starch, potato starch, pectin, agar | 5-10 | 5.00 |
| Core component mix | Dibasic calcium phosphate anhydrous | | 25-35 | 25.00 |
| Core component mix | Menthol extract | | 0.5-1 | 0.75 |
| Core component mix | Potassium hydrogen tartrate | | 2.5-7 | 5.00 |
| Active | THC extract | CBD extract, CBDa extract, THCa extract | 0.5-1.5 | 1.25 |
| Total | | | 100% | 100% | e. Dosage

The formulation may comprise about 1 to 10 mg of the active ingredient, particularly about 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10, 15, 20, 25, 30, 35, 40, 45, 50, 55, 60, 65, 70, 75, 80, 85, 90, 95, or 100 mg, or a range thereof. In one example, the active ingredient is THC, and the formulation may comprise about 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, or 10 mg, or a range thereof. In another example, the active ingredient is CBD, and the formulation may comprise about 5, 10, 15, 20, 25, 30, 35, 40, 45, 50, 55, 60, 65, 70, 75, 80, 85, 90, 95, or 100 mg, or a range thereof. In one example, the formulation comprises 5 or 10 mg THC and/or CBD extract, particularly THC extract.

3. Methods of Making Formulation

Provided herein is a method of making a formulation disclosed herein. The formulation may be manufactured at a temperature of about 68 to 72° F., and may also be manufactured at a relative humidity of about 44 to 50%. The formulation may be made by a process comprising manufacturing an active ingredient extract mix and the core component mix, and combining the active ingredient extract mix and the core component mix.

The active ingredient extract mix may be manufactured by adding the active ingredient described herein in an extract form to the excipient. The active ingredient extract may be from a medium chain triglyceride extraction. In one example, the active ingredient extract is added to silicon dioxide. In another example, the active ingredient extract is CBD and/or THC extract, which may be at a concentration of 10, 15, 20, 25, 30, 35, 40, 45, 50, 55, 60, 65, 70, 75, 80, 85, 90, 95, or 100 mg/mL of the active ingredient extract. The combined active ingredient extract and excipient may be triturated, which may ensure even absorption and distribution of the active ingredient extract in the excipient. The combined components may be sieved, which may ensure a uniform powder. In one example, the sieve is a #8 size sieve.

The core component mix may be manufactured by combining one or more core component mix components described herein. In one example, the core component mix components comprise 24 mg mannitol, 120 mg citric acid, 12 mg sodium bicarbonate, 40 mg calcium carbonate, 200 mg dibasic calcium phosphate anhydrous, 0.3 mg menthol extract, and 40 mg potassium hydrogen tartrate. The combined components may be mixed, and may further be triturated to ensure even distribution of the ingredients.

The formulation may also be manufactured by making a final mix, which may be a final tablet mix. The active ingredient extract mix may be combined with the core component mix to form the final mix, and may further be triturated to ensure even distribution of the ingredients. The final mix may be sieved, which may ensure a uniform powder. In one example the sieve is a #8 size sieve. The final mix may be pressed into a solid form, which may be a tablet. In one example, the final mix is pressed with a tablet press, which may be fitted with a 12 mm die. The final mix may be compressed for 1, 2, 3, 4, 5, 6, 7, 8, 9, or 10 minutes, particularly 1 minute, using about 10-15 kN of force. The tablet may be stored with a silica gel dessicant.

The present invention has multiple aspects, illustrated by the following non-limiting examples.

Example 1

Solid Tablet CBD Formulation

This example describes a method of producing a solid tablet described herein. In particular, the solid tablet is fast-dissolving.

Procedure

Ensure correct environment is attained prior to tablet production

Temperature: 68-72° F.

Relative humidity: 44-50%

Cannabis Extract Mix

In a 100 mL beaker, slowly add 0.25 mL of cannabis extract (40 mg/mL MCT oil extraction) to 240.0 mg of silicon dioxide Triturate the resulting mixture to ensure even absorption and distribution of cannabis extract in the silicon dioxide Sieve mixture with #8 size sieve to ensure uniform powder Inactive Ingredient Mix ("Core Component Mix")

In a separate 100 mL beaker mix the following ingredients: 24.0 mg mannitol, 120.0 mg citric acid, 12.0 mg sodium bicarbonate, 40.0 mg of calcium carbonate, 200.0 mg dibasic calcium phosphate anhydrous, 0.3 mg menthol extract, and 40.0 mg sodium citrate Combine these ingredients and triturate to ensure even distribution of components Make Final Tablet Mix Combine Cannabis Extract Mix and Inactive Mix in a 250 mL beaker.

Combine these ingredients and triturate to ensure even distribution of components.

Sieve mixture with #8 size sieve to ensure uniform powder prior to pressing tablet Feed Final Tablet Mix from previous steps into a tablet press (fitted with 12 mm die).

Compress the final tablet mixture for 1 minute using ~10-15 kN of force.

Remove tablet from tablet press and store finished tablet with a silica gel dessicant in a cool, dry place away from sunlight.

Example 2

Orally Disintegrating/Sublingual/Buccal Formulations Provide Rapid Onset of Effects This example demonstrates that oral formulations described herein provide rapid onset and peak effects of an active ingredient. The effects of exemplary oral formulations described herein were measured against a control. Subjects were assigned to receive either an active (n=7) or placebo (n=1) formulation lacking an active ingredient. The subject characteristics are described in the table below.

TABLE 2

|  | Active | Placebo |
| --- | --- | --- |
| Sex, n (%) |  |  |
| Male | 4 (50.0) | 1 (100.0) |
| Female | 3 (50.0) | 0 (0.0) |
| Mean Age, years | 34.67 +/− 11.4 | 32.0 +/− 0.0 |
| Prior Cannabis User | Yes | Yes |

The effects of the formulations were measured over a 120 minute period. No subject was lost to follow up or excluded from the analysis.

The results of the analysis are provided in FIG. 1, which shows the effects of the active over time. As shown in the figure, A=acidic ingredient, where A is citric acid, and B=basic ingredient, where B is sodium carbonate/calcium carbonate. The Y-axis=0, 1, 2, 3, 4, 5, 6, 7, 8, 9, 10, 15, 20, 25, 30, 45, 60, 75, 90, 105, and 120 minutes. Subjects reported responses at these pre-defined time points. Virtual analog scales (VAS) measured levels of "effect" (a combination of increased relaxation, altered perception, increased appetite as perceived by the user). The STANDARDIZE tool in Excel was used to bring all data to baseline. The peak effect was set as 100 for all users, so that the effects became negative for the active ingredient group if the (average of the data points for each sample)>(individual data point).

The results in FIG. 1 indicate that basic ("B") ingredients are key to improved effects. Overall, slopes demonstrate increased onset of action when using combinations of A and B. Steepest slopes are shown for 5% A/10% B, 10% A/10% B, 15% A/15% B. The slopes suggest fast onset of the effect of the active ingredient. Furthermore, 10% A/10% B had the fastest onset of peak effect at about 15-20 minutes.

The invention claimed is:

1. An oral dosage form, wherein the oral dosage form is sublingual, comprising:
    (a) about 0.5 to 3% wt/wt of a sweetener selected from the group consisting of mannitol, sorbitol, xylitol, lactitol, erythritol, and a combination thereof;
    (b) about 6.5 to 20% wt/wt citric acid, tartaric acid, or succinic acid;
    (c) about 6.5 to 20% wt/wt sodium bicarbonate, potassium bicarbonate, or potassium carbonate;
    (d) about 1 to 5% wt/wt sodium carbonate or calcium carbonate;
    (e) about 25 to 35% wt/wt silicon dioxide;
    (f) about 5 to 10% wt/wt cellulose;
    (g) about 25 to 35% wt/wt dibasic calcium phosphate anhydrous;
    (h) about 0.5 to 1% wt/wt menthol extract;
    (i) about 2.5 to 7% wt/wt potassium hydrogen tartrate; and
    (j) about 0.5 to 1.5% wt/wt active ingredient selected from the group consisting of tetrahydrocannabinol (THC) extract, cannabidiol (CBD) extract, an analog of the foregoing, a derivative of the foregoing, and a combination thereof, wherein the sublingual dosage form comprises about 5 mg to about 100 mg of the active ingredient.

2. The oral dosage form of claim 1, wherein the sweetener is mannitol.

3. The oral dosage form of claim 1, comprising citric acid.

4. The oral dosage form of claim 1, comprising sodium bicarbonate.

5. The oral dosage form of claim 1, comprising sodium carbonate.

6. The oral dosage form of claim 1, comprising silicon dioxide.

7. The oral dosage form of claim 1, comprising cellulose.

8. The oral dosage form of claim 1, wherein the menthol extract is menthol oil 0.3 mg.

9. The oral dosage form of claim 1, wherein the active ingredient comprises an ingredient selected from the group consisting of THC extract, CBD extract, tetrahydrocannabinolic acid (THCa) extract, and cannabidiolic acid (CBDa) extract.

10. The oral dosage form of claim 9, wherein the active ingredient comprises THC extract.

11. The oral dosage form of claim 1, comprising:
    (a) about 3% wt/wt mannitol;
    (b) about 15% wt/wt citric acid;
    (c) about 15% wt/wt sodium bicarbonate;
    (d) about 5% wt/wt sodium carbonate;
    (e) about 25% wt/wt silicon dioxide;
    (f) about 5% wt/wt cellulose;

(g) about 25% wt/wt dibasic calcium phosphate anhydrous;
(h) about 0.75% wt/wt menthol oil 0.3 mg;
(i) about 5% wt/wt potassium hydrogen tartrate; and,
(j) about 1.25% wt/wt THC extract.

12. The oral dosage form of claim 1, wherein the oral dosage form is effervescent when dissolved in an aqueous solution.

13. A sublingual dosage form, consisting of:
(a) 3% wt/wt mannitol;
(b) 15% wt/wt citric acid;
(c) 15% wt/wt sodium bicarbonate;
(d) 5% wt/wt sodium carbonate;
(e) 25% wt/wt silicon dioxide;
(f) 5% wt/wt cellulose;
(g) 25% wt/wt dibasic calcium phosphate anhydrous;
(h) 0.75% wt/wt menthol extract;
(i) 5% wt/wt potassium hydrogen tartrate; and
(j) 1.25% wt/wt THC extract.

14. The dosage form of claim 13, wherein the menthol extract is menthol oil 0.3 mg.

15. The dosage form of any one of claim 13, wherein the dosage form is effervescent when dissolved in an aqueous solution.

16. The oral dosage form of claim 1, comprising 0.5 to 3% wt/wt mannitol, 6.5 to 20% wt/wt citric acid, 6.5 to 20% wt/wt sodium bicarbonate, 1 to 5% wt/wt sodium carbonate, and 25 to 35% wt/wt silicon dioxide.

* * * * *